United States Patent [19]
Nelson et al.

[11] Patent Number: 5,812,261
[45] Date of Patent: Sep. 22, 1998

[54] METHOD AND DEVICE FOR MEASURING THE THICKNESS OF OPAQUE AND TRANSPARENT FILMS

[75] Inventors: Keith A. Nelson, Newton, Mass.; John A. Rogers, Castle Rock, Colo.; Matthew J. Banet, Cambridge, Mass.; John Hanselman, Needham, Mass.; Martin Fuchs, Uxbridge, Mass.

[73] Assignee: Active Impulse Systems, Inc., Natick, Mass.

[21] Appl. No.: 783,046

[22] Filed: Jan. 15, 1997

Related U.S. Application Data

[63] Continuation of Ser. No. 680,002, Jul. 15, 1996, abandoned, and a continuation-in-part of Ser. No. 350,378, Dec. 5, 1994, Pat. No. 5,633,711, and a continuation of Ser. No. 910,762, Feb. 2, 1992, abandoned.

[51] Int. Cl.[6] ........................................... G01J 3/30
[52] U.S. Cl. .................... 356/318; 356/376; 356/371
[58] Field of Search .................... 356/318, 376, 356/371

[56] References Cited

U.S. PATENT DOCUMENTS

| | | | |
|---|---|---|---|
| 4,522,510 | 6/1985 | Rosencwaig et al. | 374/4 |
| 4,728,165 | 3/1988 | Powell et al. | 350/364 |

*Primary Examiner*—David C. Nelms
*Assistant Examiner*—Reginald A. Ratliff
*Attorney, Agent, or Firm*—Fish & Richardson, P.C.

[57] ABSTRACT

A method for determining the thickness of a thin sample is described. The method includes the step of exciting time-dependent acoustic waveguide modes in the sample with an excitation radiation field. The acoustic waveguide modes are detected by diffracting probe radiation off a ripple morphology induced on the sample's surface by the acoustic waveguide modes. The diffracted probe radiation is then analyzed to measure phase velocities or frequencies of the acoustic waveguide modes. A thickness of the thin sample is determined by comparing the measured phase velocities or frequencies to the phase velocities or frequencies calculated from a mathematical model.

33 Claims, 11 Drawing Sheets

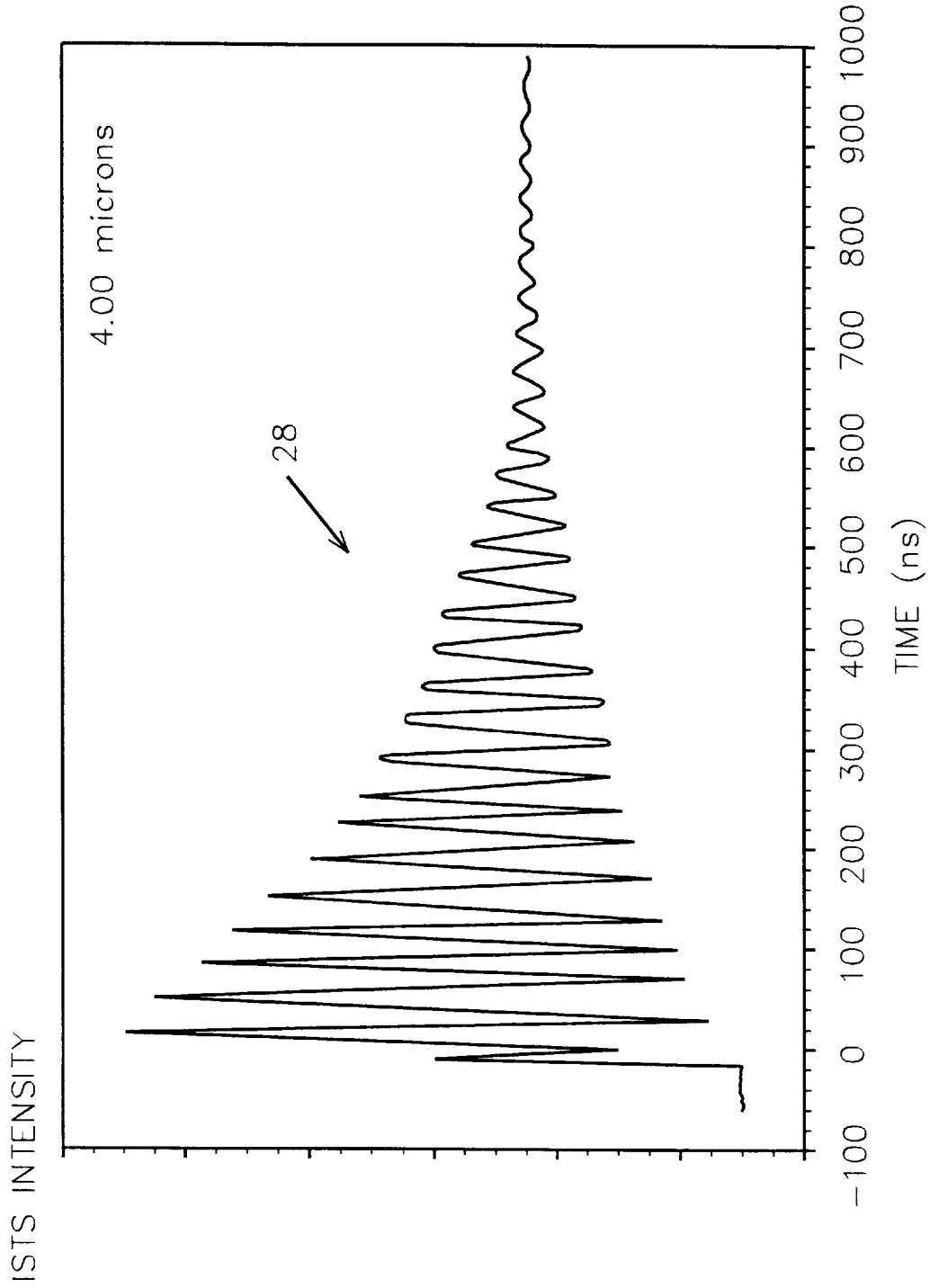

METHOD AND DEVICE FOR MEASURING THE THICKNESS OF OPAQUE AND TRANSPARENT FILMS

BACKGROUND OF THE INVENTION

This is a continuation of application Ser. No. 08/680,002, filed Jul. 15, 1996, now abandoned. This application is a continuation-in-part of U.S. Ser. No. 08/350,378, entitled "Measurement of Material Properties with Optically Induced Phonons", filed Dec. 5, 1994 now U.S. Pat. No. 5,633,711. This application also is a continuation of U.S. Ser. No. 07/910,762, now abandoned having the same name and filed Feb. 2, 1992. These applications are incorporated herein by reference.

This invention relates to methods for determining the thickness of both opaque or transparent samples (e.g., thin films).

Thin films of dielectric (e.g., polymer, oxide) and conducting (e.g., metal) materials are used in a range of microelectronic, optical, and biomedical devices. A microprocessor, for example, contains multiple layers of metal, semiconducting, and oxide thin films. Thickness variations in these films can modify the films' electrical and mechanical properties, thereby affecting the performance of the microprocessor. Accordingly, film thickness is often monitored as a quality-control parameter during and/or after the microprocessor's fabrication.

Well-known techniques, such as optical ellipsometry and interferometry, measure the thicknesses of transparent films. Measuring the thicknesses of opaque films (e.g., metal films) is a more difficult problem. Current methods for measuring metal film thickness include electrical tests and x-ray spectroscopy. In the electrical test (commonly called a sheet-resistance test), a pair of conducting probes contact the film; electrical resistance, as measured by the probes, is proportional to the film's thickness. Sheet-resistance tests require contacting the film, making such tests undesirable for measuring actual devices during the fabrication process. X-ray-based techniques measure the thickness of metal films by inducing, measuring, and analyzing x-ray fluorescence. This method is both non-contact and non-destructive, but requires large, unwieldy instruments that generate hazardous x-ray radiation.

SUMMARY OF THE INVENTION

In general, in one aspect, the invention provides a method for determining the thickness of both transparent or opaque samples (e.g., thin films within a microelectronic circuit). The method includes the step of exciting time-dependent "acoustic waveguide modes" in the sample using an excitation radiation field. The radiation field includes a spatially and temporarily varying optical interference pattern containing alternating "bright" and "dark" regions defined by a wavevector (described in detail below). Absorption of light in the bright regions launches acoustic waveguide modes that induce a ripple morphology on the sample's surface. The waveguide modes are measured by diffracting a portion of the probe radiation off the ripple morphology. The diffracted probe radiation is then detected and analyzed to yield the frequency of the acoustic waveguide modes. This property, in turn, is related to the sample's thickness.

In another aspect, the invention provides a method for determining the thickness of a thin sample by exciting and detecting time-dependent acoustic waveguide modes in the sample. Here, to increase the accuracy of the measurement, the wavevector of the acoustic waveguides modes is chosen to optimize (e.g., maximize or nearly maximize) the dependence of the frequency on the thickness of the sample. The thickness of the sample is then determined from the frequency.

Several techniques are used to analyze the acoustic waveguide modes to determine the sample's thickness. For example, the acoustic frequencies can be compared to a database that correlates frequency to sample thickness. This type of database is generated by measuring and recording the acoustic frequencies from standards that include films having known thicknesses.

Alternatively, the sample's thickness is determined by comparing the acoustic properties to a mathematical model. The model describes the stiffness (i.e., elastic moduli) and thickness of each layer in a multi-layer film/substrate structure, and can be used to analyze single or multiple-frequency measurements. For the multiple-frequency measurements, the exciting, detecting, and analyzing steps are repeated to generate a "dispersion" containing multiple frequencies, each corresponding to a different wavevector. The determining step of the method is an iterative fitting procedure that includes: i) proposing initial components of a stiffness tensor and an initial thickness of the sample; ii) calculating an initial dispersion based on the proposed initial components of the stiffness tensor and the initial thickness; iii) comparing the calculated dispersion to the measured dispersion; iv) repeating the proposing, calculating, and comparing steps until the calculated dispersion matches the measured dispersion to a desired degree; and, v) determining the thickness of the sample from the calculated dispersion. If the components of the stiffness tensor are known, only the thickness needs to be varied during the fitting procedure. Using the above-mentioned determining step, a single frequency can be compared to a model of a single or multi-layer film/substrate structure to calculate film thickness.

Any property that can be calculated from the frequency can be used in place of frequency during the steps described above. For example, a phase velocity (i.e., the frequency divided by the excitation wavevector) can be used in the calculations.

Samples having a range of thicknesses and compositions can be measured with the method of the invention. The sample can be, for example, thin films of metals, polymers, semiconductors, or oxides having thicknesses ranging from 100 angstroms to 20 microns. The product of the wavevector of the excitation field and the thickness of the sample is typically between about 0.1–10. The sample can be included in a device as an "outer" layer (i.e., having an exposed planar surface) or "underlying" layer (i.e., having no exposed planar surfaces) in a film/substrate structure.

The method of the invention is carried out using a film-measuring instrument that includes excitation and probe lasers for generating, respectively, a pulse of excitation radiation (at a wavelength that is strongly absorbed by the sample) and probe radiation (at a wavelength that is not substantially absorbed by the sample). Each pulse of the excitation radiation is typically focused as an elliptical spot having a major axis along the direction of the wavevector; optical interference between these spots generates the spatially and temporally varying excitation field. The probe radiation spot is typically round and covers an area which is about an order of magnitude smaller than the excitation field spot size. Each excitation pulse typically has a duration less than 1 nanosecond, while the probe radiation is typically cw radiation or a pulse having a duration longer than a lifetime of the acoustic waveguide mode (e.g., greater than about 500 nanoseconds).

The film-measuring instrument includes an optical system oriented to receive the pulse of radiation from the excitation laser, and then separate the pulse into at least two optical pulses. The system delivers the pulses to the sample so that they interfere and form the optical interference pattern within or on top of the sample. This launches the acoustic waveguide modes which, in turn, generate the ripple morphology on the sample's surface. The probe radiation is oriented to diffract off of the ripple morphology to form a diffraction signal which is then monitored with an optical detector (e.g., a fast photodiode having a response time faster than 1 nsec). In this way, a light-induced signal indicating the frequency or phase velocity of the acoustic waveguide mode is generated and analyzed to determine a thickness of the thin sample.

The excitation laser is a typically a Nd:YAG, Nd:YLF, or nitrogen laser. The probe laser is typically a cw laser, such as a gated diode laser.

The invention has many advantages. For example, the film-measuring instrument can be a stand-alone unit, or can be attached directly to a film-formation tool (e.g., a chemical-vapor deposition tool, a plasma-vapor deposition tool, a cluster tool, or a vacuum chamber) or a film-processing tool (e.g., a chemical-mechanical polisher). In this embodiment, the film-formation tool includes an optical port (e.g., a glass window) that is transparent to the excitation and probe radiation. Thus, during operation, the film-measuring instrument is oriented so that the excitation and probe radiation, and the diffraction signal, pass through the optical port. In this mode of operation, the instrument remotely measures films undergoing processing at both high and low temperatures. The instrument also functions in-line during semiconductor wafer processing to determine the exact thicknesses of metal, oxide, polymer, and semiconductor films, or to determine if thicknesses of these films are out of specification. In one embodiment, for example, the film-measuring instrument alerts a process controller when unacceptable films are being fabricated, and sends signals that correct fabrication parameters (e.g., temperature). This process can be repeated iteratively until films having the desired thickness are formed. Because film-formation processes are directly and non-invasively monitored, the instrument increases device yields, removes defective product from the fabrication process, and, in general, facilitates production of high-quality films.

The film thickness-measuring instrument collects practically noise-free data in a real-time, non-destructive, and non-contact manner. Data from a single measurement point (having an area of between 10 and 100 microns) are typically collected in less than one second and used to determine a film's thickness to within tens of angstroms. For typical film thicknesses (e.g., 1 micron) this corresponds to a fraction of a percent of the film's true value. The instrument is also compact, occupying a footprint of about 2 square feet.

Other features, aspects, and advantages of the invention follow from the following detailed description, and from the claims.

BRIEF DESCRIPTION OF THE DRAWINGS

FIG. 2 is a plot of a time-dependent diffracted signal measured with the instrument of FIG. 1A;

DETAILED DESCRIPTION OF THE INVENTION

Figure 1A:
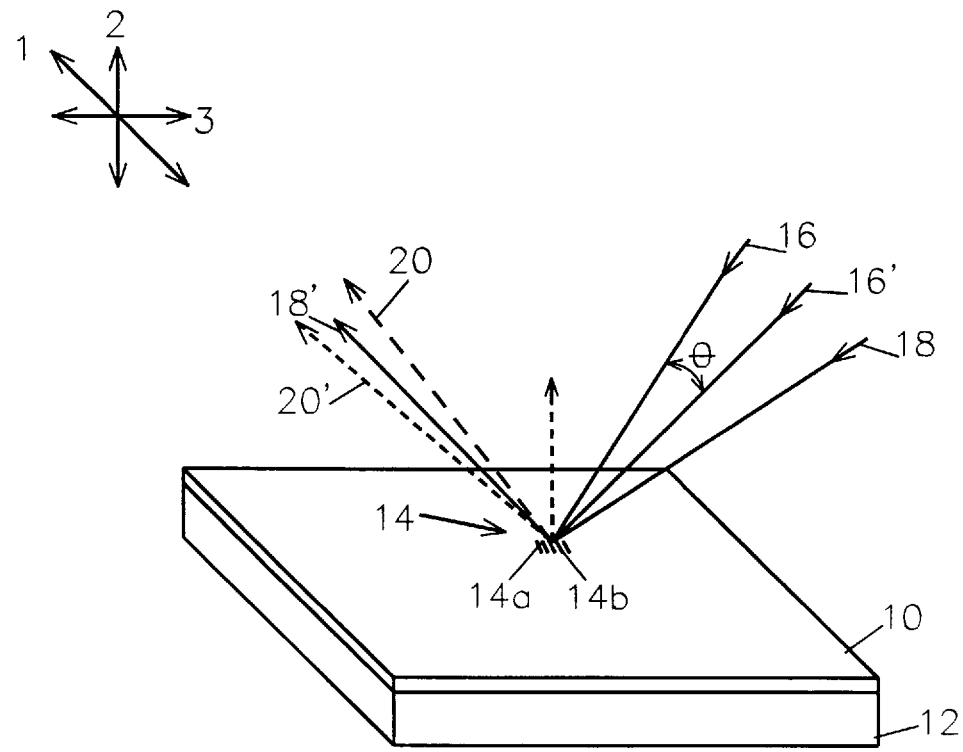
FIG. 1A is a schematic drawing showing the optical beam configuration of the film-thickness instrument according to the invention.
Figure 1B:
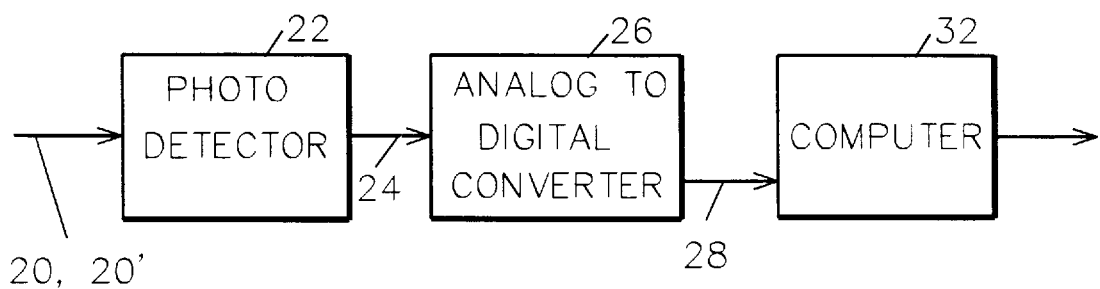
FIG. 1B is a block diagram showing a series of electrical components for measuring the signal generated by the instrument of FIG. 1A.

In FIGS. 1A and 1B, a thickness of a thin film 10 on a substrate 12 is measured by irradiating the film 10 with two excitation pulses 16, 16' and a probe pulse 18. The excitation pulses 16, 16' are short in duration (e.g., less than 1 nanosecond), are of the same wavelength, and are separated by an angle θ; the probe pulse is relatively long (e.g., several hundred microseconds). In this conventional four-wave mixing geometry, the excitation pulses are overlapped in time and space so that they interfere to form a spatially and temporally varying excitation radiation field 14 in or on the surface of the film 10. The field 14 is composed of a series of periodic, sinusoidal "bright" 14a (i.e., constructive interference) and "dark" 14b (destructive interference) regions. The direction of the field is defined by a wavevector that is inversely proportional to the spatial distance between consecutive bright (or dark) regions. The magnitude (q) of the wavevector is determined by the angle θ between the excitation pulses and the wavelength $\lambda_I$ of each pulse using the equation $q=4\pi\sin(\theta/2)(\lambda_I)^{-1}=2\pi/\Lambda$, where $\Lambda$ is the grating wavelength.

The excitation radiation field 14 excites acoustic waveguide modes in the film 10 that have a wavelength and orientation corresponding to the excitation wavevector. Excitation of the waveguide modes occurs via Impulsive Stimulated Thermal Scattering ("ISTS"), a technique that relies upon the bright regions of the excitation radiation field 14 being absorbed by the film. Heat is deposited in the film during the short duration of the pulse, causing the heated regions of the film to thermally expand. This launches coherent, counter-propagating acoustic waveguide modes having a velocity that is proportional to the mode's frequency divided by the excitation wavevector. The waveguide modes induce a morphology in the film that generates a time-dependent "ripple" on the film's surface. The frequency of the ripple oscillations depends on the thickness of the film.

The probe pulse 18 has a duration that is longer than the lifetime of the acoustic waveguide mode. During operation, the probe pulse 18 irradiates the ripple induced on the surface of the film and diffracts to form at least two signal beams 20, 20'. The ripple modulates each signal beam according to the time dependence of the acoustic waveguide modes. One of these beams is detected using a high-bandwidth photodetector 22 to generate a light-induced signal 24 that is digitized with a high-bandwidth analog-to-digital converter 26 to produce a digitized waveform signal 28 (shown, for example, in FIG. 2). The signal 28 is then sent to a computer 32 and analyzed with the wavevector of the excitation radiation field. The frequency of the waveform signal 28 is determined using standard computer algorithms, such as a fast Fourier transform algorithm. Both the frequency and wavevector are then processed by the computer to determine the film's thickness as described below.

Determination of Film Thickness

As indicated by FIG. 2, the digitized waveform signal 28 oscillates at the frequency of the detected acoustic waveguide mode. These oscillations undergo a time-dependent decrease in intensity due to damping (i.e., viscosity-related losses) in the film. At longer times (not shown in the figure) the signal includes a component that decays exponentially due to diffusion of heat in the film. The thickness of the film is determined by analyzing one or more acoustic waveguide mode frequencies.

The film's thickness is proportional to the frequency of the waveguide mode: as the film becomes thinner, its acoustic response is affected by both the underlying substrate and film layers. For example, an aluminum film supported by a relatively stiff silicon substrate will support a relatively high acoustic frequency compared to a free-standing aluminum film. Similarly, the effective stiffness of the supported film is increased as the thickness is decreased. The frequency of the acoustic waveguide mode increases with the stiffness of the film. Conversely, a thicker aluminum film takes on less of silicon's acoustic properties, and thus supports relatively low-frequency acoustic waveguide modes.

The thickness of each layer in the sample is determined explicitly from a single-frequency measurement or by measuring acoustic waveguide mode frequencies at a number of different wavevectors (i.e., a dispersion). Either the single frequency or dispersion is then calculated using a mathematical model that describes a multi-layer film/substrate structure with a $(4n \times 2) \times (4n \times 2)$ determinant (where n is the number of film layers) and an iterative fitting procedure (e.g., a non-linear least squares fitting algorithm, such as a Marquardt-Levenburg algorithm). The determinant is defined by imposing the appropriate boundary conditions at the film/air and film/substrate interfaces. Each layer described by the determinant is characterized by a thickness and a stiffness tensor component.

Figure 3:
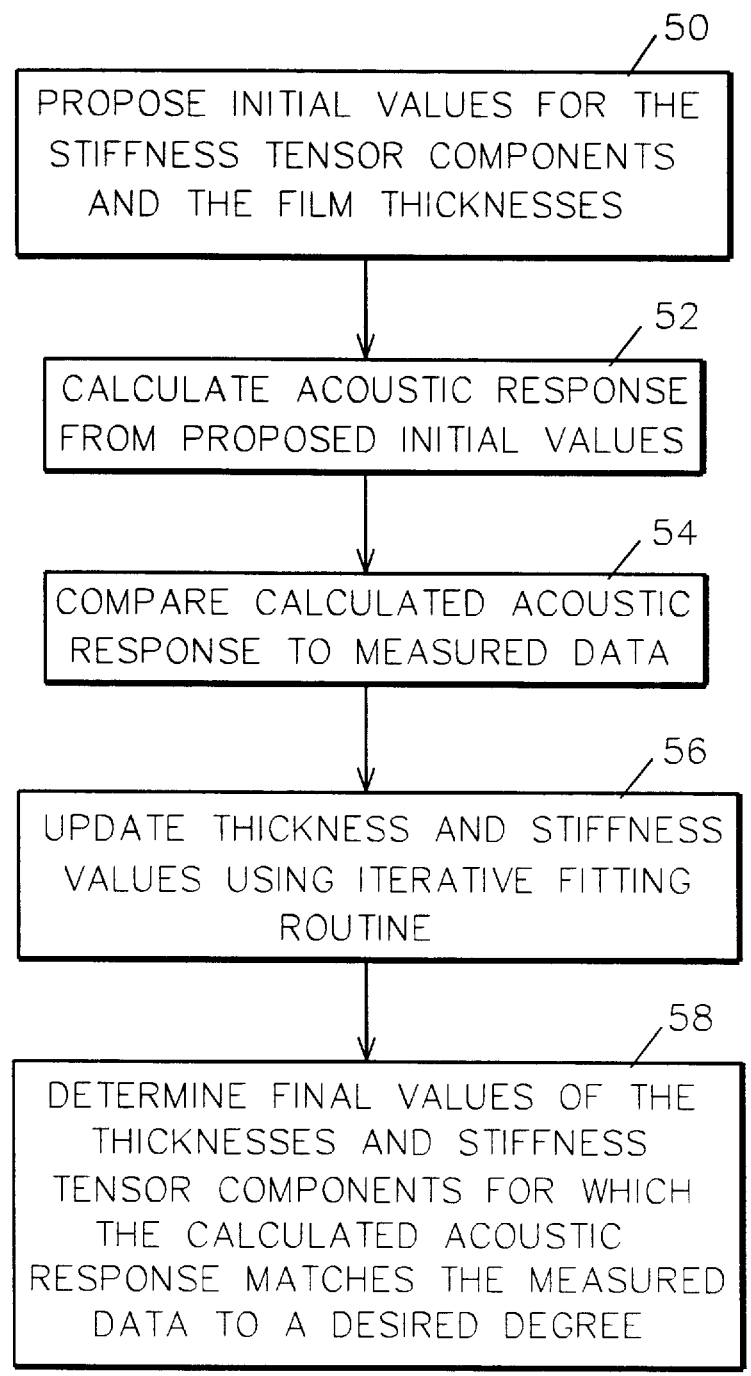
FIG. 3 is a flow chart showing a method for calculating film thickness according to the invention.

Referring to FIG. 3, film thickness is determined from the dispersion by proposing initial values for both the stiffness tensor components and the film thicknesses (step 50). In most cases, the stiffness tensor components are known and are therefore fixed during the fitting procedure. The acoustic response of each film is then calculated from the proposed values (step 52) and compared to the measured data (step 54). The thickness and stiffness values can be updated using the iterative fitting routine (step 56). The final values of the thicknesses and stiffness tensor components are found when the calculated acoustic response matches the measured data to a desired degree (step 58).

The mathematical model used in the iterative fitting routine is derived from the acoustic field equations as described, for example, in M. Grimsditch et. al, Phys. Rev. Lett. 58:1216 (1987). The general differential equation for the model is:

$$\rho \frac{\partial^2 u_i}{\partial t^2} - c_{ijkl} \frac{\partial^2 u_k}{\partial x_j \partial x_l} = 0 \qquad (1)$$

where $\rho$ is the density, $u_i$ is the displacement in dimension i, and c is a stiffness tensor containing elements $c_{ijkl}$.

In this analysis, the coordinate system is defined such that the wavevector points in the z direction (direction index 3, shown in FIG. 1A as being in the plane of the film). Next, the x and z dimensions (directions 1 and 3, respectively) are assumed to extend infinitely. These assumptions are valid experimentally. The excitation pulses are cylindrically focused to produce an elliptical spot such that the major axis of the focus is much longer than the fringe spacing. In this way, the motions in the z direction are assumed to be purely sinusoidal. Moreover, the probe radiation spot size is small compared to that of the excitation radiation. The derivatives along x can thus be ignored. Finally, the tensor elements $c_{ijkl}$ are not independent from one another because of the physical constraints of the film/substrate system. These elements can therefore be written in reduced form as $c_{ij}$. With these simplifications, the equations of motion can be written as:

$$\rho \frac{\partial^2 u_y}{\partial t^2} - c_{11} \frac{\partial^2 u_z}{\partial y^2} - c_{44} \frac{\partial^2 u_z}{\partial z^2} - (c_{23} + c_{44}) \frac{\partial^2 u_z}{\partial y \partial z} = 0 \qquad (3a)$$

$$\rho \frac{\partial^2 u_z}{\partial t^2} - c_{44} \frac{\partial^2 u_z}{\partial y^2} - c_{11} \frac{\partial^2 u_z}{\partial z^2} - (c_{23} + c_{44}) \frac{\partial^2 u_z}{\partial y \partial z} = 0 \qquad (3b)$$

where the c's are elements of the stiffness tensor. This expression can be written in tensor matrix form:

$$c_{ij} = \begin{vmatrix} c_{11} & c_{12} & c_{13} & 0 & 0 & 0 \\ c_{21} & c_{22} & c_{23} & 0 & 0 & 0 \\ c_{31} & c_{32} & c_{33} & 0 & 0 & 0 \\ 0 & 0 & 0 & c_{44} & 0 & 0 \\ 0 & 0 & 0 & 0 & c_{44} & 0 \\ 0 & 0 & 0 & 0 & 0 & \frac{1}{2}(c_{11} - c_{22}) \end{vmatrix} \qquad (4)$$

The above equations are manipulated by taking a Laplace transform along t, a Fourier transform along z, and postulating solutions to $u_y$ and $u_z$ of the form, respectively, $\sim\exp(iqby)$ and $\sim\exp(iqbz)$, where b is unknown and of the same value for both solutions, and q is the wavevector described above. The resulting equations are used to form a $(4n \times 2) \times (4n \times 2)$ determinant, where n is the number of film layers. A bisection interval search is performed for the value of b that causes the determinant to equal zero. The process is repeated iteratively by adjusting the thickness of each layer (and any non-fixed stiffness tensor components) using the non-linear least squares fitting algorithm. The resulting set of tensor elements and thickness are compared to the data to determine the quality of the fit.

Acousto-Optical Response of Thin Films

Figure 4:
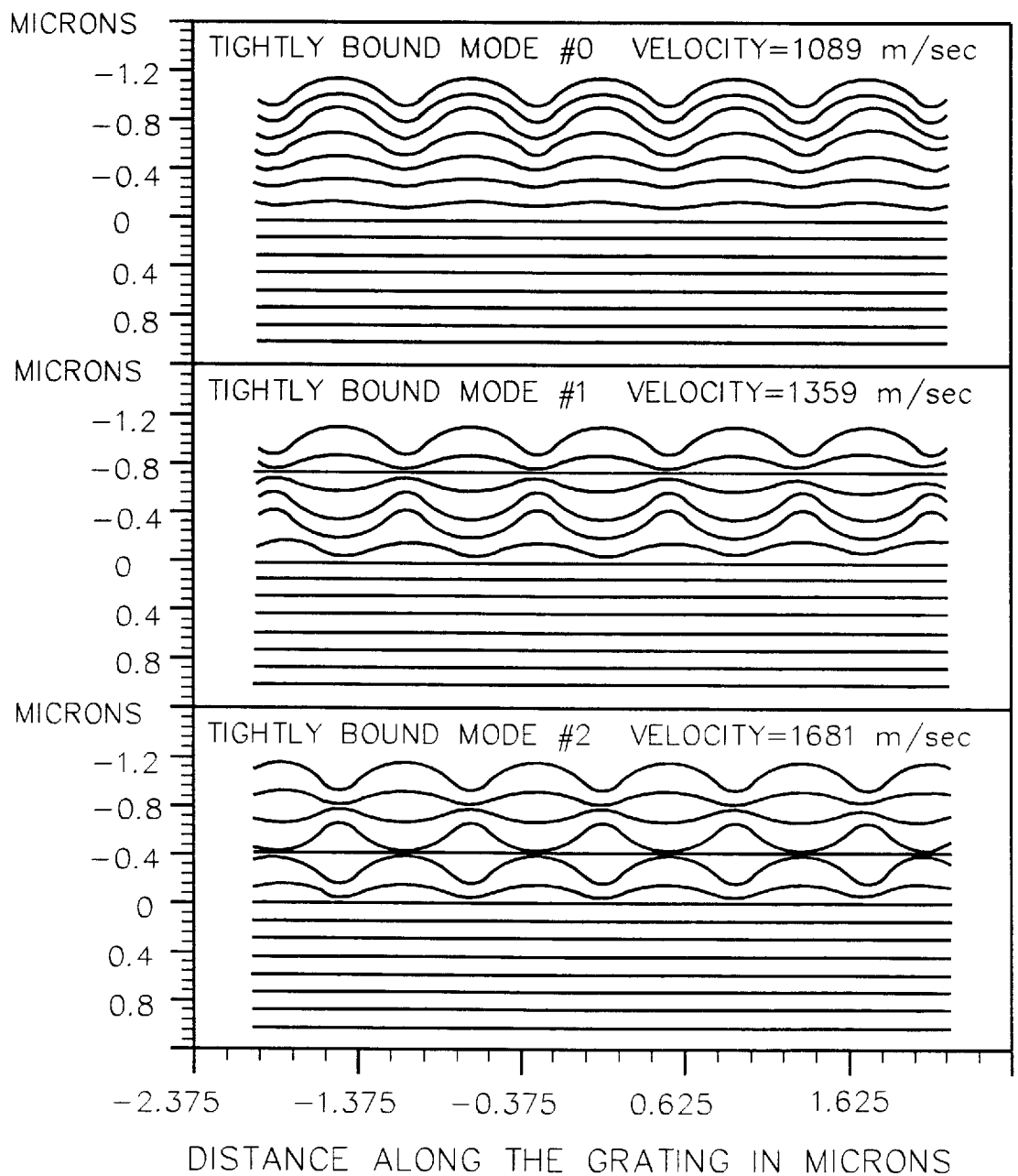
FIG. 4 is a grid-distortion diagram of the three lowest waveguide modes (modes 0–2) in a typical thin film.

FIG. 4 illustrates the thickness-dependent material displacements induced in a supported thin film by the film-measuring instrument described above. The three grid-distortion diagrams in the figure show the displacements and velocities associated with the lowest-order waveguide modes (modes 0–2). More than one of these modes can be excited simultaneously with a single excitation field. As shown by the spatially varying grid pattern, the acoustic waveguide modes in the film result in surface ripple having different spatial characteristics. When irradiated with the probe pulse, the ripple diffracts radiation to generate the signal beams (20 and 20' in FIG. 1A). These beams are then detected and analyzed to determine the properties of the film.

Figure 5A:
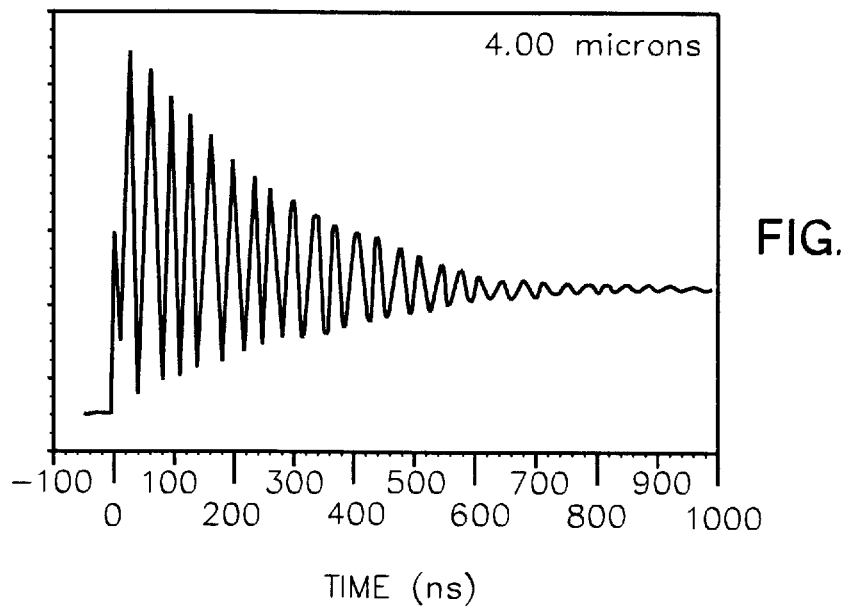
FIGS. 5A–5C are plots of the time-dependent diffracted signals measured in, respectively, a 4-micron fluorinated polymer film, a 5-micron fluorinated polymer film, and both the 4 and 5-micron polymer films.
Figure 5B:
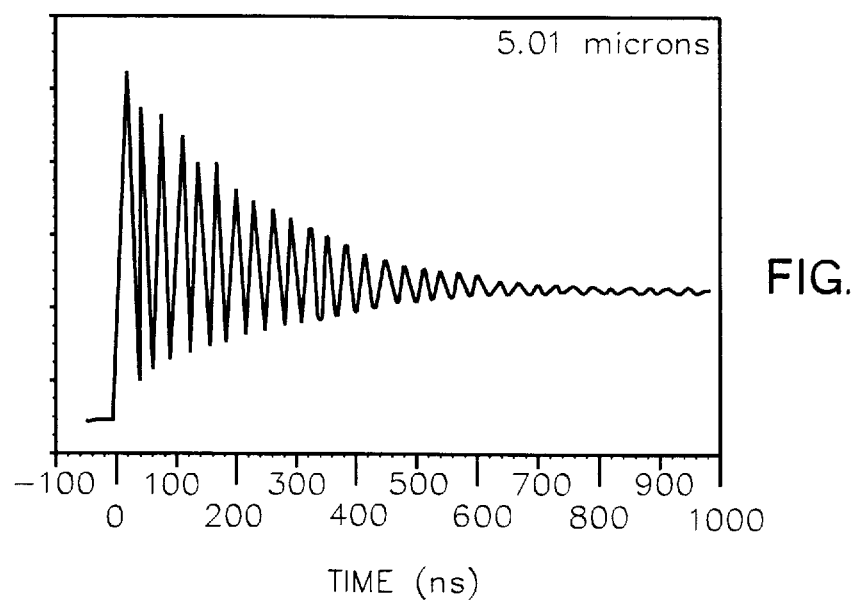
Figure 5C:
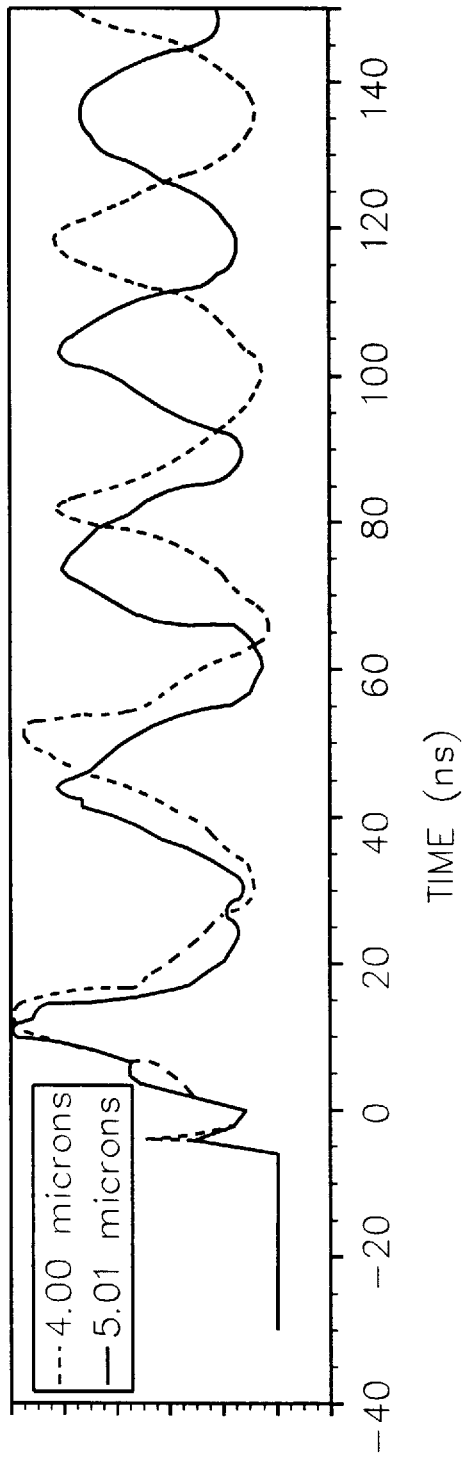
Figure 6:
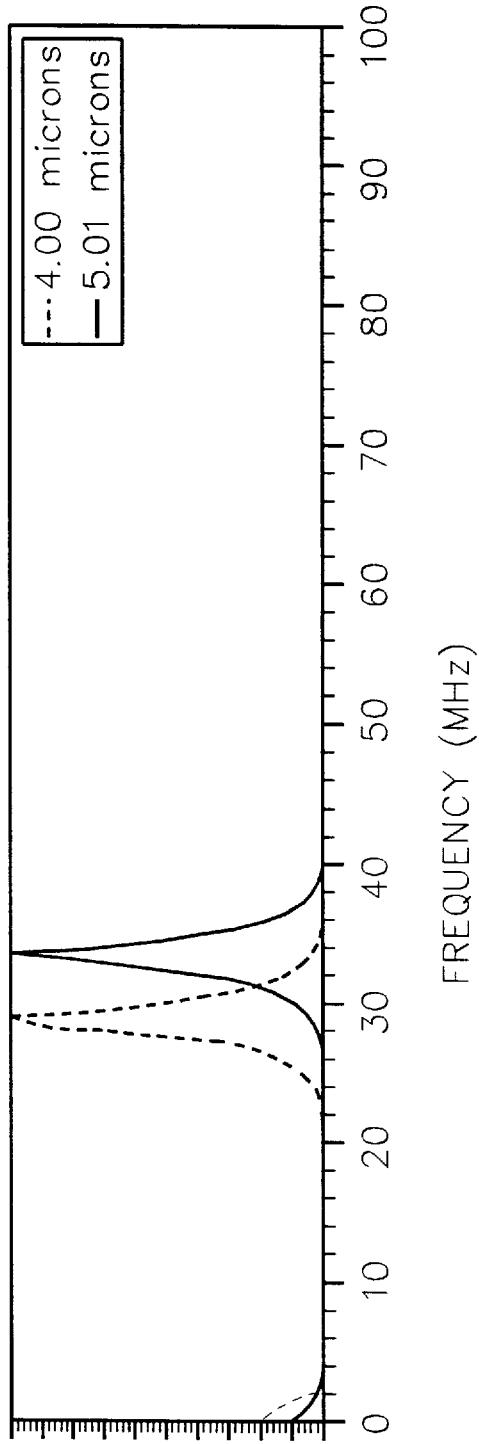
FIG. 6 is a plot of the Fourier transforms of the data of FIG. 5A–5C.

FIGS. 5A–5C indicate generally how the time-dependent response of the lowest-order acoustic waveguide mode (mode 0 of FIG. 3) of a thin film varies as a function of film thickness. The film-measurement instrument described above was used to excite the lowest-order acoustic waveguide modes in thin films composed of a fluorinated polymer sample. The signals shown in FIGS. 5A and 5B were measured from films having thicknesses of, respectively, 4.0 and 5.0 microns (as measured with a stylus profilometer). Although the data shown in these figures appear to be similar, closer inspection (FIG. 5C) indicates that the frequencies measured from the two films are, in fact, significantly different. FIG. 6 shows the Fourier transforms of the time-dependent data shown in the plots of FIGS. 5A and 5B. As is clear from these frequency-domain data, the 4-micron film supports a frequency of about 28 MHz, whereas the 5-micron film supports a frequency of about 32 MHz.

Figure 7A:
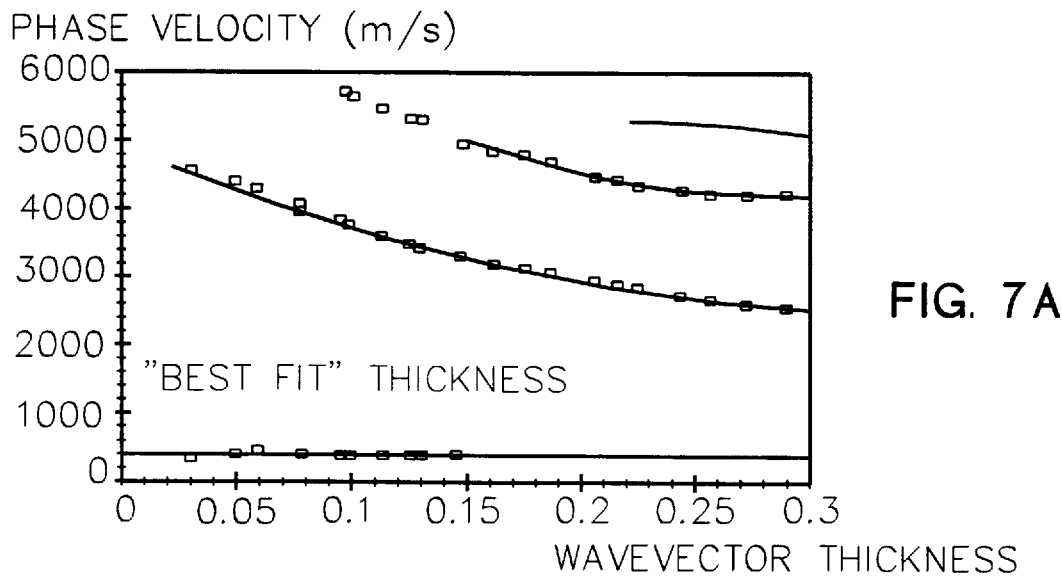
FIGS. 7A–7C are plots of dispersion curves measured from a 127-nm hafnium film on silicon dioxide and silicon fitted using, respectively, the "best fit" thickness, a thickness 10% larger than the "best fit" thickness, and a thickness 10% smaller than the "best fit" thickness.
Figure 7B:
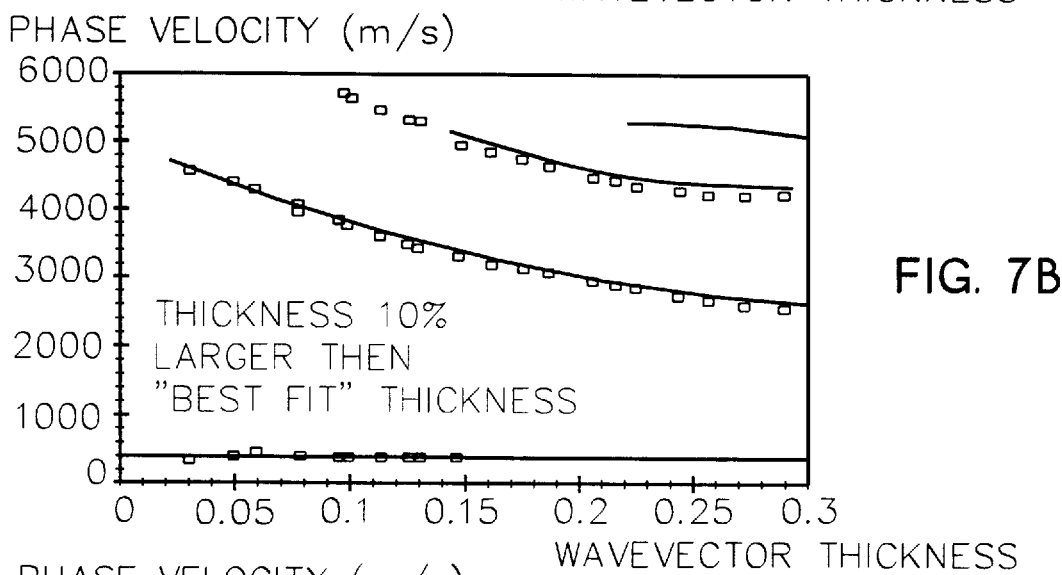
Figure 7C:
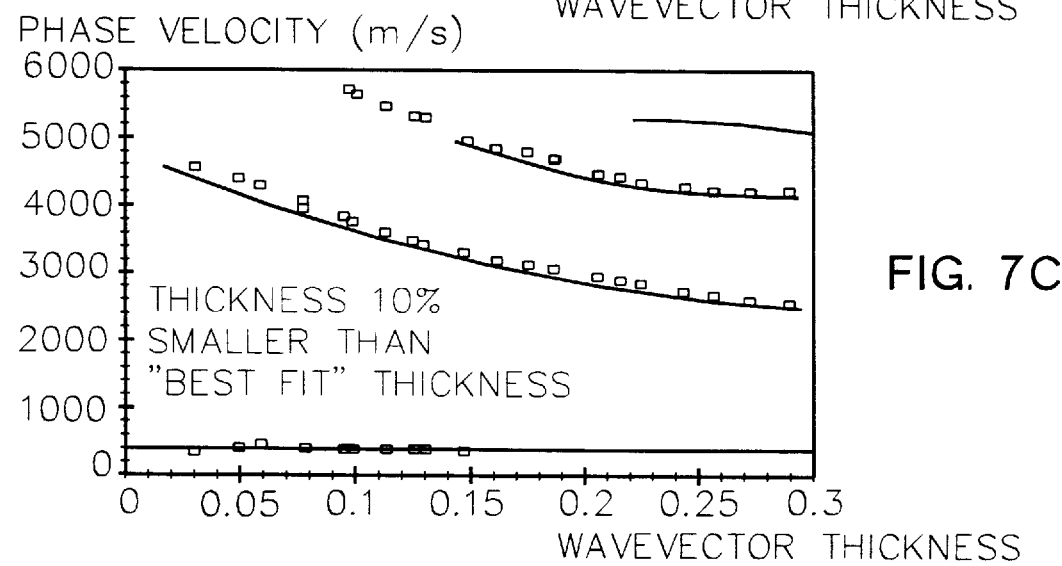

FIGS. 7A–7C show the dispersion (i.e., phase velocity plotted as a function of excitation wavevector for the four lowest-order acoustic modes) and corresponding fits for a 127-nm hafnium film deposited on a silicon oxide layer on a silicon substrate. The squares in the figures indicate data points measured using the film-measuring instrument; the solid lines are the fits to the data generated using the mathematical model described above. The data indicate the sensitivity of the fits to film thickness. Compared to the "best fit" thickness (FIG. 7A), a thickness that is increased or decreased by 10% yields computed results lying, respectively, above (FIG. 7B) or below (FIG. 7C) the experimentally determined data. Closer analysis of the experimental data and the corresponding fits indicates that a thickness value that differs from the "best fit" value by only a few percent clearly falls outside the data.

Figure 8:
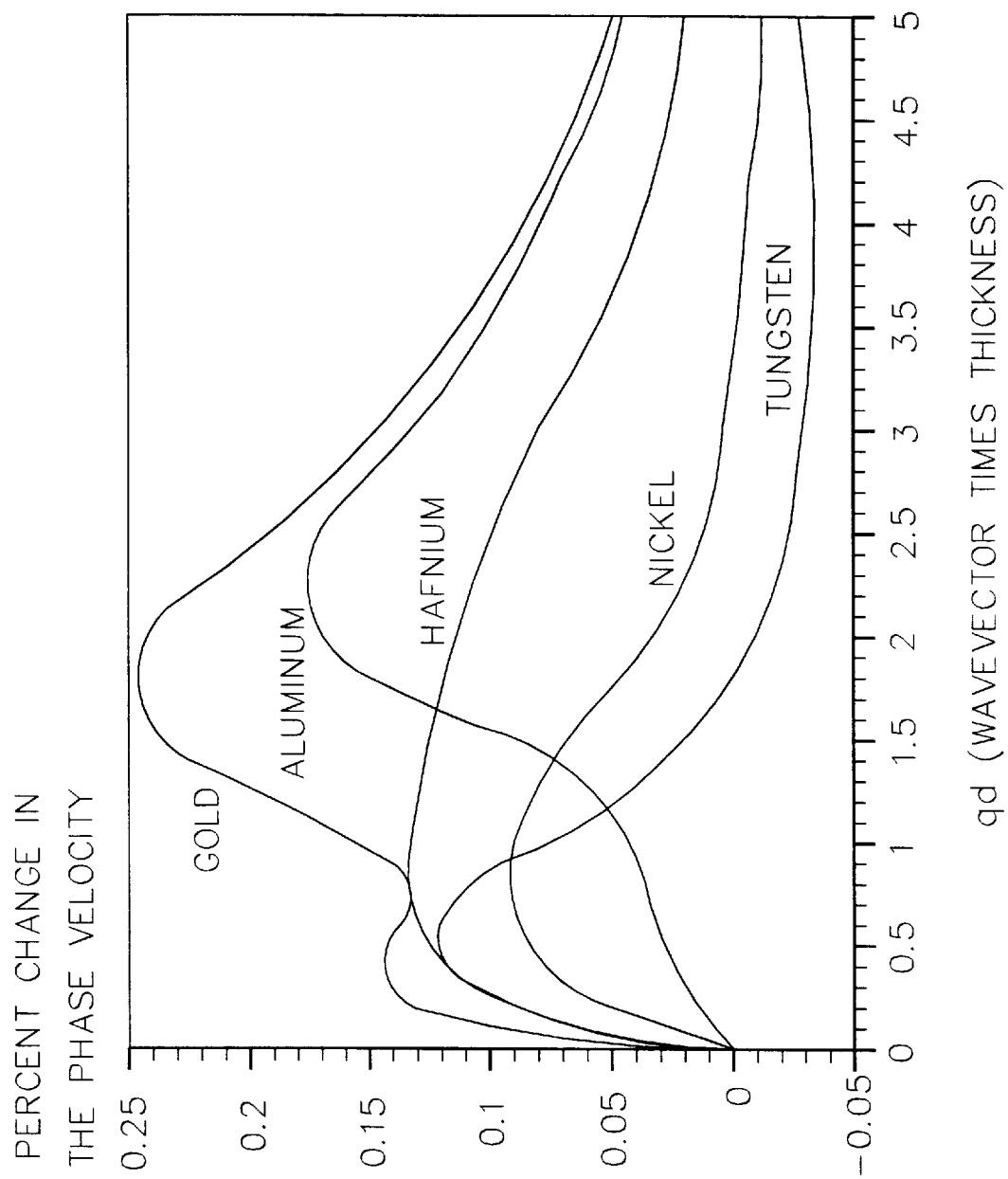
FIG. 8 is a plot of the calculated change in phase velocities of gold, aluminum, hafnium, nickel, and tungsten films as a function of the wavevector-thickness product when the film thickness is changed by 0.5%.

FIG. 8 indicates how the frequencies of the lowest-order acoustic waveguide mode vary with film thickness. To calculate the curves shown in the figure, the thicknesses of a number of different metal films deposited on silicon were changed (using a computer simulation) from their base values by 0.5%. The phase velocity for each metal film was then calculated according to the mathematical model similar to the one described above. As is clear from the data, the phase velocity supported by each metal film is most sensitive to the thickness change at different wavevector-thickness products. For example, the phase velocity of gold is most sensitive to the thickness change at a wavevector-thickness product of about 1.5. At this value, a change in thickness results in a relatively large (and thus relatively easy-to-measure) change in phase velocity. The corresponding values for aluminum, hafnium, nickel, and tungsten are, respectively, about 2.0, 0.75, 0.6, and 0.5.

As is clear from FIG. 8, it is desirable to choose an excitation wavevector so that the wavevector-thickness product of the film maximizes the dependence of the film's phase velocity on thickness. When this condition is met, small changes in the film's thickness will result in relatively large changes in the measured phase velocity. Using this technique, the accuracy of the film-thickness measurement is easily maximized.

Optical System

The excitation light source used in the film-measuring instrument is typically a pulsed Nd:YAG laser that is Q-switched, mode-locked, or both. A particularly desirable excitation light source is a microchip laser, such as is described in U.S. Pat. No. 5,394,413. The pulse duration of the excitation radiation field must be short enough to impulsively stimulate material motions in the film via ISTS, and is typically between 50 picoseconds (ps) and 5 nanoseconds (ns). The output pulse typically has an energy of between 0.1 and 40 millijoules, and a wavelength of 1064 nm. The second (i.e., 532 nm), third (i.e., 355 nm), or even higher harmonics of this laser can also be generated and used to excite the sample. These lower wavelengths may be used if the film's optical properties (i.e., reflectivity or absorbtivity) at 1064 nm are not adequate to excite the acoustic modes.

The excitation pulses should have a wavelength at which greater than 20% of the light is absorbed by the film. In typical applications, the excitation radiation field is completely absorbed in the first 10–20 nm of the film to effectively excite the lowest-order mode. Too little absorption (i.e., too much reflection or transmission) may result in insufficient excitation of the acoustic waveguide modes. The wavevector of the excitation radiation field is such that the wavevector-thickness product is typically in the range of 0.1–10.0.

The probe radiation is typically derived from a single-mode diode laser producing between 0.1 and 1 Watt in the visible or infrared frequency range. The probe radiation typically has a wavelength that is not absorbed by the film. In order to measure the entire time dependence of the acoustic and thermal responses induced in the sample (which, e.g., may take place over several hundreds of microseconds), a well-defined probe waveform is generated by electro-optically modulating the cw probe radiation with a light modulator that controls both the duration and shape of the probe waveform. For example, a square probe pulse can be generated that has a time duration which is slightly longer than the time-dependent excited motions in the film (e.g., between 1 and 20 microseconds). The probe pulse may also be a Q-switched laser pulse having a long duration relative to the sample's acoustic response. Both the cw and Q-switched probe pulses are advantageous, as they can be used to measure the entire acoustic response with a single laser shot (i.e., real-time data acquisition), and therefore obviate the need for optical delay lines. This dramatically reduces both the time required for measuring data and the size of the film-measuring instrument.

The probe radiation is typically focussed to a spot size that is smaller than the spot size of the excitation radiation field. In particular, the excitation pulses are typically cylindrically focused to produce an excitation radiation field having an elliptical shape, with the major axis of the ellipse along the direction of the wavevector and being much larger than the fringe spacing of the excitation radiation field.

In addition, the repetition rate of the pulses must be high enough to allow suitable data averaging (when necessary), but low enough to allow the film's temperature to return to ambient temperature between laser shots. The repetition rate is typically between 1 and 2000 Hz, with the rate being adjusted for measurement of different types of films. For films that easily damage, it is desirable to reduce the repetition rate of the excitation laser. This decreases heat-related effects which can potentially damage thin, fragile films.

Once detected, the light-induced waveform signal typically has a signal-to-noise ratio greater than 100:1. The signal-to-noise ratio can be further enhanced by signal averaging at a rate which is limited only by the repetition rate of the laser (typically around 1 kHz) or the speed of the recording electronics (typically on the order of a millisecond). Signal averaging can improve the signal-to-noise ratio to greater than 500:1; data-collection times for averaged signals are still in the range of several seconds.

Any optical system can be used to direct the excitation and probe pulses onto the sample. One such system, for example, is described in U.S. Ser. No. 08/377,310, Rogers et al., entitled "Simplified Device and Method for Time-resolved Optical Measurements", filed Jan. 24, 1995, the contents of which are incorporated herein by reference. The optical system described in this reference includes a 'phase mask' that diffracts a single, incident excitation beam into two spatially diverging beams; the angle of divergence is determined by a diffracting pattern on the phase mask. Using a lens, the diverging beams are recombined and imaged onto a sample's surface, where they interfere to form an excitation pattern having a well-defined wavevector. Excitation patterns having different wavevectors are formed simply by translating the phase mask to move different diffracting patterns into the excitation beam's path.

The optical system containing the phase mask has a number of advantages. In particular, the phase mask reduces the number of optical components (e.g., lenses, beamsplitters, and mirrors) required to deliver the excitation beams to the sample. This, in turn, reduces the size of the optical system. Moreover, the phase mask is the only moving part in the optical system, and can be easily translated using conventional, computer-controlled automation systems. This means that the optical system can be completely automated and can operate for long periods of time without requiring user intervention.

The Apparatus

Figure 9:
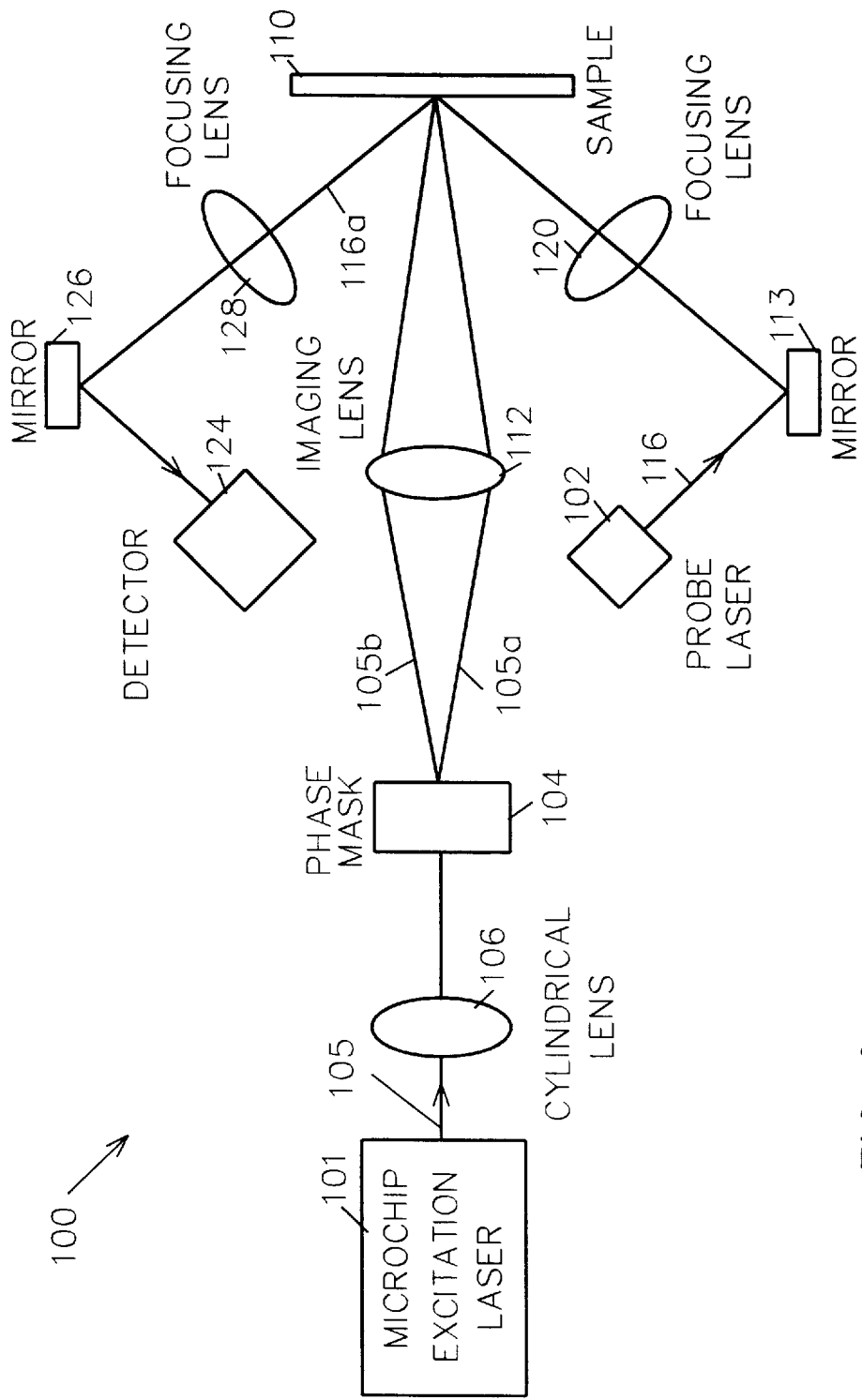
FIG. 9 is a schematic drawing of the optical components of a small-scale, compact film-measuring instrument.

The optical and electrical components of the film-measuring instrument can be disposed in a number of different configurations. FIG. 9 shows one such instrument 100 containing a microchip excitation laser 101 (such as the Nd:YAG microchip laser described in U.S. Pat. No. 5,394,413), high-power, cw-diode probe laser 102, and phase mask 104. In this particular configuration, the sizes of both the excitation and probe lasers are dramatically reduced. Moreover, the use of cw, real-time detection and the phase mask minimizes the required number of optical components. Taken in combination, these features significantly decrease the instrument's 'footprint', resulting in a compact, portable, small-scale spectrometer for measuring samples using the four-wave mixing technique. The instrument 100 shown in FIG. 9, for example, has a footprint of about 1 square foot, whereas conventional, large-scale four-wave mixing spectrometers typically have a footprint of about 20 square feet.

During operation, the microchip excitation laser 101 generates a single excitation beam 105 that is focused onto the phase mask 104 using a cylindrical lens 106. A diffraction pattern on the phase mask 104 splits the incident beam 105 into two components 105$a$, 105$b$ which are then imaged onto a sample 110 using an imaging lens 112. This forms an excitation radiation pattern which, in turn, excites acoustic waveguide modes on the sample's surface. The entire duration of the waveguide modes is measured by irradiating the waveguide modes with a cw beam 116 from the diode probe laser 102. The cw beam 116 is directed onto the sample using a first mirror 118 and first focusing lens 120, and is diffracted to form a signal beam 116$a$. The signal beam 116$a$ is then directed onto a photodetector 124 using a second mirror 126 and focussing lens 128. The photodetector 124 must have a high bandwidth (e.g., 1 GHz) to time resolve the individual features of the signal beam and collect data in real time.

Figure 10:
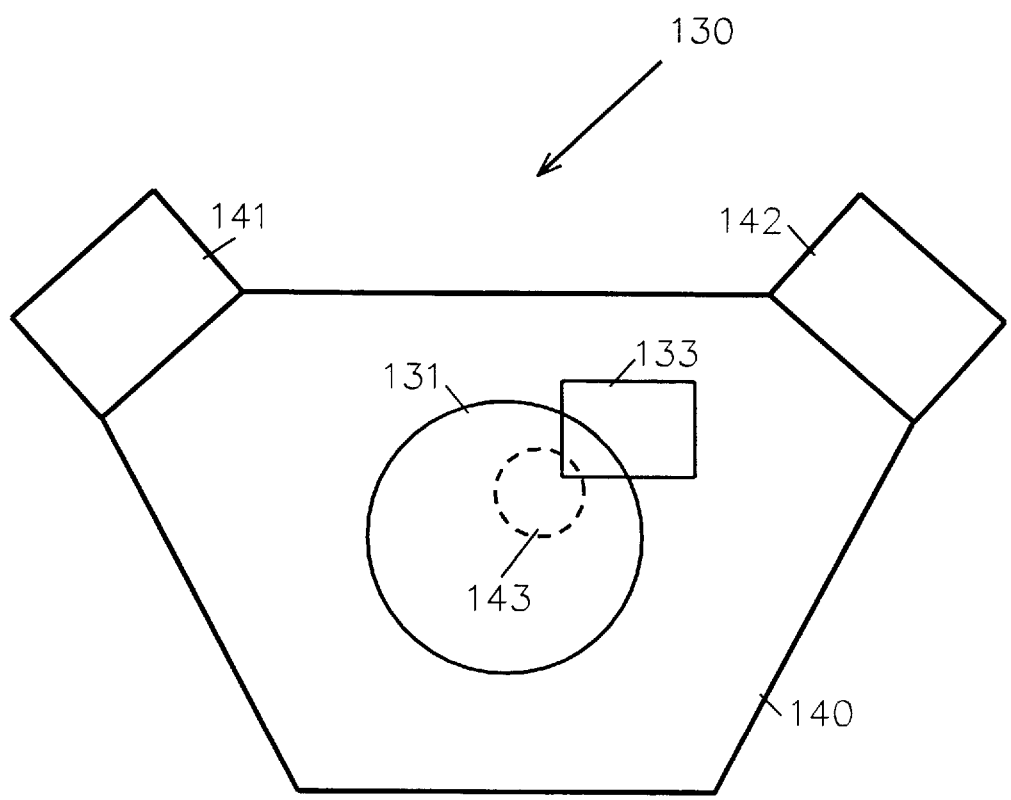
FIG. 10 is a top schematic view of a film-measuring instrument attached to a film-processing tool.

Because of its small footprint and ability to collect data in real-time, the film-measuring instrument shown in FIG. 9 can be attached directly to a film-formation tool (e.g., a chemical-vapor deposition tool, a plasma-vapor deposition tool, a cluster tool, or a vacuum chamber) or a film/substrate processing tool (e.g., a chemical-mechanical polisher) and used as a process monitor. Referring to FIG. 10, a film-formation tool 130 includes a central housing 140 containing an optical port 131 and multiple film-processing chambers 141 and 142 (e.g. metal deposition and etch chambers). During operation, a film-containing device 143 (e.g. processed wafer) is robotically transferred under vacuum from the film-processing chamber 142 to the central housing 140. The optical port 131 is transparent to both the excitation and probe radiation. The film-measuring instrument 133 is attached to the film-formation tool 131 above the optical part 131, and is positoined so that during operation the excitation and probe radiation, and the resulting diffraction signal, pass through the optical port 131. In this way, the instrument 133 remotely measures films being processed by the film-formation tool 130. The film-measuring instrument 133 can generate a signal indicating the quality of the film. This signal can then be sent to the film-processing chamber 142 or to the operator so that appropriate adjustments can be made to the process. The instrument can therefore be used in-line during semiconductor wafer processing to determine the thicknesses of metal, oxide, polymer, and semiconductor films. The instrument can also be used as a simple quality-control device for determining whether or not a film is within a manufacturer's specifications.

Other Embodiments

Figure 11:
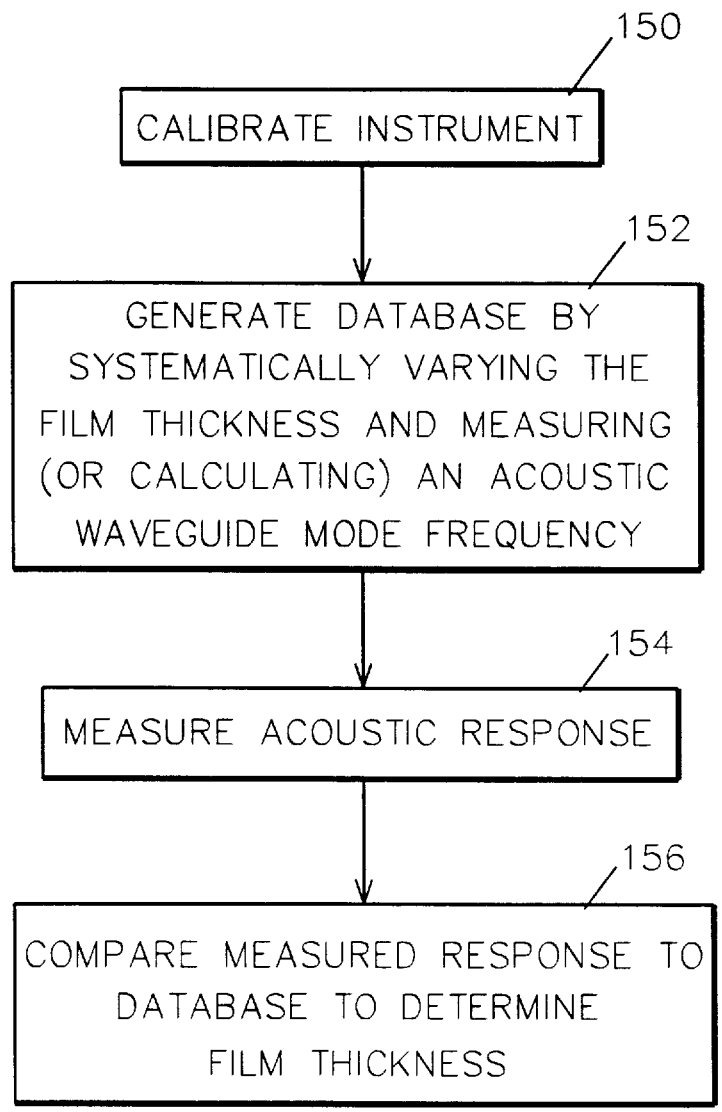
FIG. 11 is a flow chart showing a method for calculating film thickness according to an alternate embodiment of the invention.

Other embodiments are within the scope of the invention. Referring to FIG. 11, the thickness-measuring instrument can be calibrated so that a single acoustic frequency is converted into a film thickness without having to compare the measured data to a mathematical model (step 150). The instrument is calibrated, for example, by measuring the frequency of waveguide modes from standard samples where the thicknesses and compositions of the top and underlying layers are known. A database is then generated by systematically varying the thickness of the film in the standard, measuring (or calculating) an acoustic waveguide mode frequency, and then storing each thickness and the correlated frequency in the database (step 152). During a measurement of a sample of known composition but unknown thickness, the acoustic frequency is measured (step 154) and compared to the database (step 156) to determine the film's thickness.

This same type of calibration-based measurement determines the thicknesses of underlying film layers. For example, the film-measuring instrument can be calibrated against multi-layer standards containing layers with known thicknesses and compositions. As before, a database is generated by systematically varying the thickness of each layer in the standard, measuring (or calculating) an acoustic waveguide mode frequency, and then correlating each thickness of each underlying layer to the frequency of the acoustic waveguide mode. During an actual measurement, an acoustic waveguide mode frequency is measured from a multi-layer sample and compared to a database generated using the appropriate standard to determine the thicknesses of the sample's underlying layers.

Acoustic waveguide modes in transparent films can be excited via mechanisms other than ISTS, such as by Impulsive Stimulated Brillion Scattering (ISBS). ISBS is described in more detail in Y. X. Yan, J. Chem. Phys., Vol. 87, p. 6240–6257 (1987).

Light sources other than Nd:YAG lasers may be used to optically excite the film. Suitable lasers include, among others, Nd:YLF, nitrogen, ion (e.g., argon and krypton), Ti:Sapphire, diode, $CO_2$, holmium, excimer, dye, and metal-vapor lasers. Typically, these lasers are electro-optically or acousto-optically modulated (using, e.g., mode-locking and Q-switching devices known in the art) to produce suitable energies (i.e., between 0.1 and 100 microjoules/pulse) and pulse durations (i.e., less than about 1 ns).

Similarly, light sources other than diode lasers may be used as the probe laser. Alternative lasers include ion, quantum-well, and Nd:YAG lasers. Alternatively, a pulsed laser producing a pulse duration greater than about 500 ns may be used as the probe laser. Pulsed light sources which may be used to generate the probe pulse include Q-switched Nd:YAG, Nd:YLF, Ti:Sapphire, diode, $CO_2$, holmium, excimer, diode, dye, and metal-vapor lasers.

Still other embodiments are within the scope of the following claims.

What is claimed is:

1. A method for determining the thickness of a thin layer which forms part of a sample, comprising:

exciting time-dependent acoustic waveguide modes in the sample by directing an excitation radiation field defined by a wavevector onto the sample;

detecting the acoustic waveguide modes by diffracting probe radiation off a ripple morphology induced on the sample's surface by the acoustic waveguide modes;

analyzing the diffracted probe radiation to measure at least one velocity or frequency of the acoustic waveguide modes; and, determining the thickness of the thin layer from the measured phase velocity or frequency.

2. The method of claim 1, wherein said determining comprises calculating the thickness from the measured phase velocity or frequency and a mathematical model.

3. The method of claim 2, wherein the mathematical model is calculated from the equation of motion:

$$\rho \frac{\partial^2 u_i}{\partial t^2} - c_{ijkl} \frac{\partial^2 u_k}{\partial x_j \partial x_l} = 0$$

where $\rho$ is the density, $u$ is the displacement, c is the stiffness tensor, and the coordinate system is defined with the wavevector in the plane of the thin sample.

4. The method of claim 1, wherein said exciting, detecting, and analyzing are repeated to generate a dispersion comprising multiple phase velocities or frequencies, each corresponding to a different wavevector.

5. The method of claim 4, wherein said determining comprises:

proposing initial components of a stiffness tensor and an initial thickness of the thin sample;

calculating an initial dispersion from the proposed initial components of the stiffness tensor and the initial thickness;

comparing the calculated initial dispersion to the measured dispersion;

repeating said proposing, calculating, and comparing until the calculated dispersion matches the measured dispersion to a desired degree; and, determining the thickness of the layer for which the calculated dispersion matches the measured dispersion to the desired degree.

6. The method of claim 1, wherein said determining includes comparing the measured phase velocities or frequencies to a database containing phase velocities or frequencies correlated to a layer thickness.

7. The method of claim 6, wherein the database is generated by measuring the frequencies or velocities of acoustic waveguide modes from standards comprising thin layer having known thicknesses.

8. The method of claim 1, wherein the thin layer is an outer-lying film and has an exposed planar outer surface and an unexposed surface attached to a substrate or underlying thin layer.

9. The method of claim 1, wherein the thin layer is an under-lying film having no exposed planar surfaces.

10. The method of claim 1, wherein greater than 20% of the excitation radiation field is absorbed by the sample.

11. The method of claim 1, wherein the thin layer is a metal, polymer, oxide, or semiconducting thin film.

12. The method of claim 1, wherein the probe radiation is generated by temporally modulating an output of a cw laser to produce a probe pulse.

13. The method of claim 12, wherein the duration of the probe pulse is longer than a lifetime of the acoustic waveguide mode.

14. The method of claim 1, further comprising comparing the determined thickness of the thin layer with at least one previously determined property to monitor the quality of the thin layer.

15. A method for determining the thickness of a thin layer that forms part of a sample, comprising:

exciting time-dependent acoustic waveguide modes in the sample by directing two time-coincident laser pulses onto the sample so that they overlap in an excitation region and interfere to form an excitation radiation field having a known wavevector;

detecting the acoustic waveguide modes by directing probe radiation onto the excitation region so that it is diffracted, the probe radiation having a temporal width that is comparable to the detectable presence of said time-dependent acoustic waveguide modes; and analyzing the diffracted probe radiation to determine a measured phase velocity or frequency of the acoustic waveguide modes to determine the thickness of the thin layer.

16. A film-measuring instrument for determining the thickness of a thin layer which forms part of a sample, comprising:

a first excitation laser source for generating a pulse of excitation radiation;

an optical system oriented to receive the pulse of radiation from the excitation laser, separate the pulse into at least two optical pulses, and deliver the pulses to the sample so that they interfere within or on top of the sample to induce an acoustic waveguide mode which induces a ripple on a surface of the sample;

a second, probe laser source for generating probe radiation oriented to irradiate and diffract off of the ripple induced on the surface of the sample to form a diffraction signal;

a detector for detecting the diffraction signal to generate a frequency or phase velocity of the acoustic waveguide mode; and an analyzer to determining a thickness of the layer from the frequency or phase velocity of the acoustic waveguide mode.

17. The instrument of claim 16, further including an optical detector for detecting and time resolving the diffraction signal.

18. The instrument of claim 17, wherein the optical detector has a response time faster than 1 nsec.

19. The instrument of claim 16, wherein the excitation radiation is a pulse having a duration less than 1 nanosecond, and the probe radiation is a pulse having a duration of less than 1 millisecond.

20. The instrument of claim 16, wherein the excitation laser is a Nd:YAG, Nd:YLF, or nitrogen laser.

21. The instrument of claim 16, wherein the probe laser is a continuous-wave laser.

22. The instrument of claim 21, wherein the probe laser is a diode laser or a diode-pumped laser.

23. A film-formation system for depositing a thin layer on a sample, comprising:
   a film-formation tool; and
      a film-measuring instrument attached directly to said film-formation tool, said film-measuring instrument comprising:
      a first excitation laser source for generating a pulse of excitation radiation;
      an optical system oriented to receive the pulse of radiation from the excitation laser, separate the pulse into at least two optical pulses, and deliver the pulses to the sample so that they interfere within or on top of the sample to induce an acoustic waveguide mode which induces a ripple on a surface of the sample;
      a second, probe laser source for generating probe radiation oriented to irradiate and diffract off of the ripple induced on the surface of the sample to form a diffraction signal;
      a detector for detecting the diffraction signal to generate a frequency or phase velocity of the acoustic waveguide mode; and
      an analyzer to determining a thickness of the thin layer from the frequency or phase velocity of the acoustic waveguide mode.

24. The system of claim 23, wherein the film-formation tool comprises an optical port which is transparent to the excitation and probe radiation generated in the film-measuring instrument.

25. The system of claim 24, wherein the film-measuring instrument attached to the film-formation tool is oriented so that the excitation and probe radiation, and the diffraction signal, pass through the optical port.

26. The system of claim 24, wherein said film-formation tool is a chemical-vapor deposition tool, a plasma-vapor deposition tool, a cluster tool, a chemical-mechanical polisher, or a vacuum chamber.

27. A method for determining the thickness of a thin layer which forms part of a sample, comprising:
   exciting and detecting time-dependent acoustic waveguide modes that create a ripple morphology on the surface of the sample, the waveguide modes characterized by a frequency and a wavevector, where the wavevector is chosen to optimize or nearly optimize the dependence of the frequency on the thickness of the layer; and
   analyzing the frequency to determine the thickness of the layer.

28. The method of claim 27, wherein the wavevector is chosen to maximize or nearly maximize the dependence of the frequency on the thickness of the layer.

29. The method of claim 2, wherein the thickness is calculated using the measured frequency and a density and sound velocity in the mathematical model.

30. The method of claim 1, wherein the metal film comprises aluminum or tungsten.

31. The instrument of claim 16, wherein the analyzer calculates the thickness from the measured phase velocity or frequency and a mathematical model.

32. The method of claim 1 wherein the thin layer is a topmost layer of the sample.

33. The method of claim 1 wherein the thin layer is an underlying layer in a multilayer structure.

* * * * *